United States Patent [19]

Cox, Jr.

[11] Patent Number: 5,065,772
[45] Date of Patent: Nov. 19, 1991

[54] INFLATABLE CERIVICAL PESSARY

[75] Inventor: James E. Cox, Jr., Oxnard, Calif.

[73] Assignee: Inamed Corporation, Carpinteria, Calif.

[21] Appl. No.: 421,202

[22] Filed: Oct. 13, 1989

[51] Int. Cl.⁵ .......................... A61F 6/16; A61F 6/18
[52] U.S. Cl. .................................. 128/836; 128/839; 128/840
[58] Field of Search ............... 128/830, 833, 834, 836, 128/839–840, 401; 606/191–193

[56] References Cited

U.S. PATENT DOCUMENTS

| | | | |
|---|---|---|---|
| 705,285 | 7/1902 | Overton | 128/841 |
| 2,041,424 | 5/1936 | McCormick et al. | 128/841 |
| 2,553,428 | 5/1951 | Sokolik | 128/841 |
| 2,638,093 | 5/1953 | Kulick | 606/192 X |
| 3,154,077 | 10/1964 | Cannon | 606/192 |
| 3,401,689 | 9/1968 | Greenwood | 128/840 X |
| 3,480,017 | 11/1969 | Shute | 606/193 |
| 4,137,922 | 2/1979 | Leininger et al. | 606/193 |
| 4,237,893 | 12/1980 | Michaels | 128/839 X |
| 4,284,074 | 8/1981 | Shaw Jr. | 128/833 |
| 4,686,985 | 8/1987 | Lottick | 606/192 |

FOREIGN PATENT DOCUMENTS

| | | | |
|---|---|---|---|
| 553467 | 2/1958 | Canada | 128/836 |
| 597426 | 5/1934 | Fed. Rep. of Germany | 128/840 |
| 882288 | 3/1955 | Fed. Rep. of Germany | 128/836 |
| 960761 | 3/1957 | Fed. Rep. of Germany | 128/839 |
| 106035 | 8/1924 | Switzerland | 128/840 |

*Primary Examiner*—Robert A. Hafer
*Assistant Examiner*—Kevin G. Rooney
*Attorney, Agent, or Firm*—Donald D. Mon

[57] ABSTRACT

A cervical pressary having a central stem with a passage from end to end thereof. A distal retainer is provided at the distal end of the stem, and a proximal retainer at the other end. The retainer are flexible and distensible. They are connected to each other through the stem passage, and are inflatable by fluid injected into them. A leaflet-type fill valve passes through the wall of the proximal retainer. Th fill valve closes when outside pressure is exerted on the leaflets. The fill valve can be physically opened by insertion of a fill tube into it.

5 Claims, 2 Drawing Sheets

FIG. 6
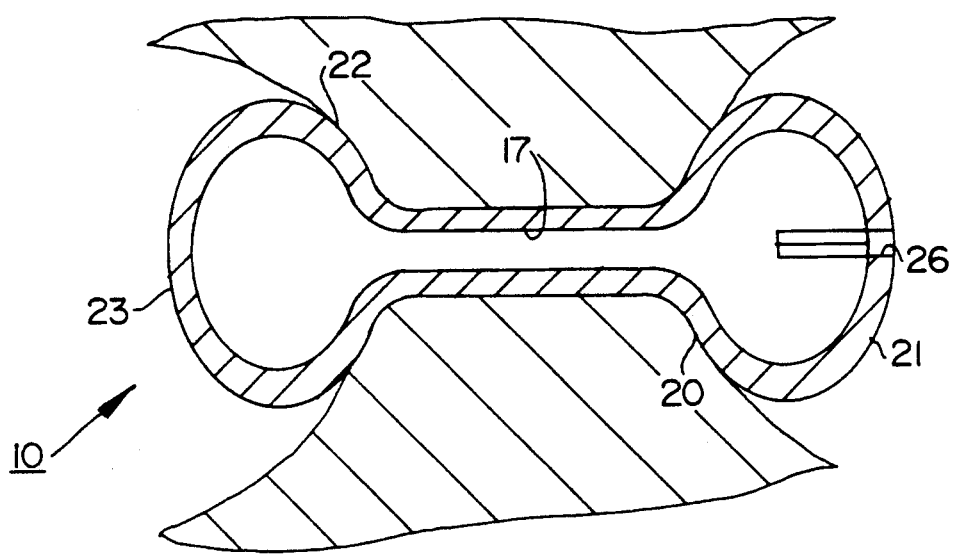
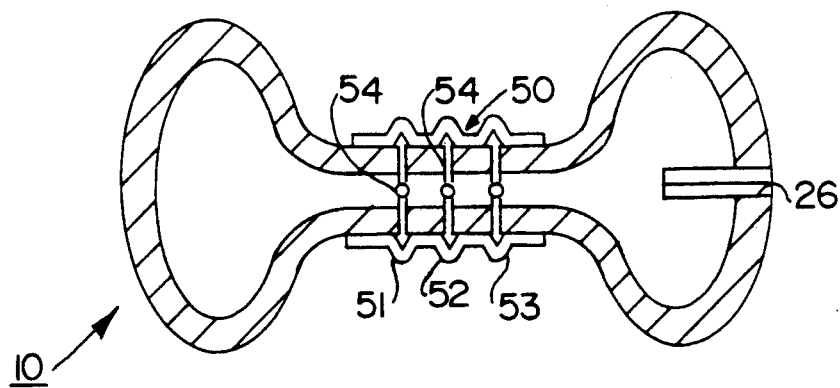
FIG. 7

5,065,772

INFLATABLE CERIVICAL PESSARY

FIELD OF THE INVENTION

This invention relates to pessaries which are inserted into and are retained in the cervix to prevent conception.

BACKGROUND OF THE INVENTION

Cervical pessaries have long been proposed as a means to prevent conception. The theory is that when properly proportioned and inserted in the cervical neck, they will prevent conception by preventing passage of sperm into the uterus.

The problem presented is straightforward. The neck of the cervix is tubular, and various techniques have been proposed to close it. One is to provide an external cap. Another is to fill the lumen of the neck to prevent flow between the device and the wall. Yet another is to cap the inner end of the neck. Some devices have proposed using two or even all three of these techniques.

It is a matter of at least mild surprise that in view of the theoretically perfect reliability of such a device, and of the elegant simplicity of its design and function, it is not generally a popular choice.

It does, of course, have its limitations. For one it must be removed monthly to enable menstrual flow to occur. Thus, insertion and removal are regularly necessary, and at least the insertion does require care and skill beyond those required by some other conventional devices.

Further, some women require reassurance that the device is properly in place. In some known devices this assurance is not available.

It is an object of this invention to provide an easily inserted pessary which is reliably retained, and whose functionality can readily be ascertained by its wearer whenever she wishes to have reassurance, thereby to produce a more acceptable product.

BRIEF DESCRIPTION OF THE INVENTION

A pessary according to this invention includes a central hollow stem with a passage from end to end. At its distal end it connects to a distal inflatable retainer. At its proximal end it connects to a proximal inflatable retainer. The retainers are fluidly connected to one another through the passage in the stem.

A fill valve is provided in the wall of the proximal retainer, adapter to receive a fill tube. The fill tube is dimensioned so it can be thrust through the fill valve and through the stem passage so as to stretch the deflated distal retainer and force it through the neck of the cervix. The fill tube is then partially withdrawn, and fluid to inflate the retainers is injected into the pessary through it. When the pessary is properly filled and the retainers are properly inflated, the fill tube is withdrawn. The fill valve closes and the pessary is emplaced.

Removal can be accomplished by inserting the fill tube through the fill valve and withdrawing fluid to deflate the pessary, which then can be pulled out with little effort.

According to a preferred feature of this invention, the fill valve is a leaflet valve wherein reverse pressure forces the leaflets together to close the valve against leakage. It is opened by inserting the fill tube through the leaflets, enabling fluid to flow in either direction through the fill tube.

According to a preferred but optional feature of the invention, the wall of the proximal inflatable retainer is so proportioned and arranged as to be noticeably distended when the pessary is filled. This condition can readily be ascertained digitally, to the reassurance of its wearer.

The above and other features of this invention will be fully understood from the following detailed descritpion and the accompanying drawings, in which:

BRIEF DESCRIPTION OF THE DRAWINGS

FIG. 6 is an axial cross-section of the embodiment of FIG. 1 in its emplaced, inflated condition; and FIG. 7 is an axial cross-section showing a variation of the embodiment of FIG. 1.

DETAILED DESCRIPTION OF THE INVENTION

Figure 1:
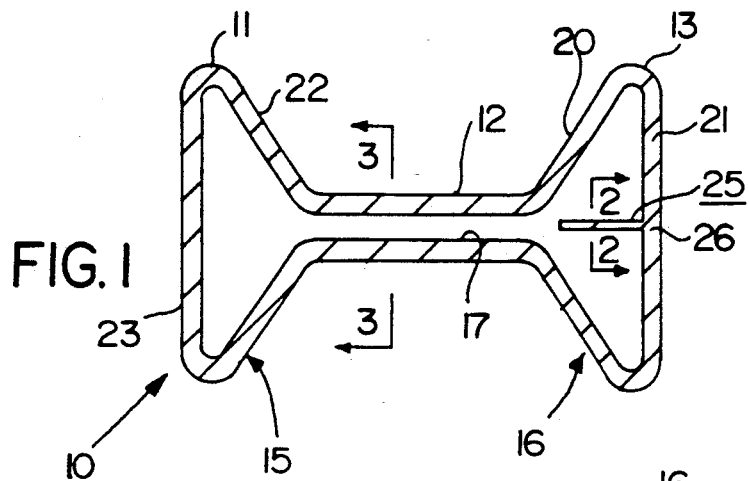
FIG. 1 is an axial cross-section of the presently-preferred embodiment of a pessary according to the invention.
Figure 4:
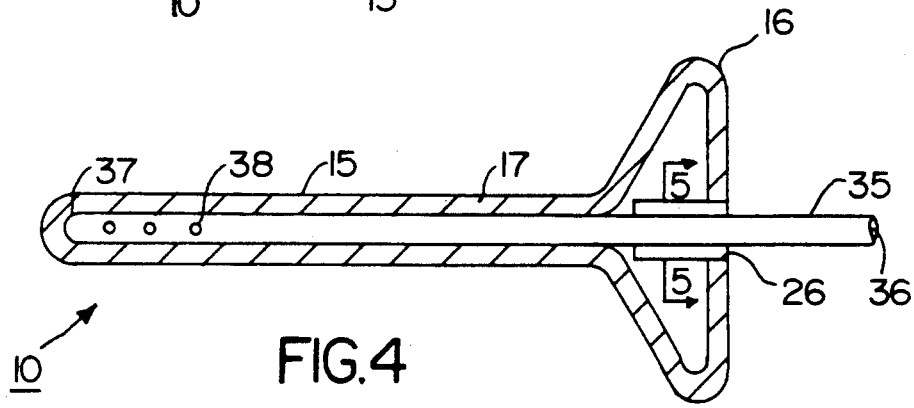
FIG. 4 is an axial cross-section of the embodiment of FIG. 1 in its insertion configuration.
Figure 2:
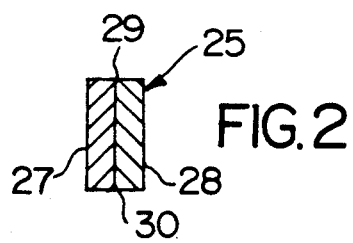
FIG. 2 is a cross-section taken at line 2—2 in FIG. 1.
Figure 3:
FIG. 3 is a cross-section taken at line 3—3 in FIG. 1.
Figure 5:
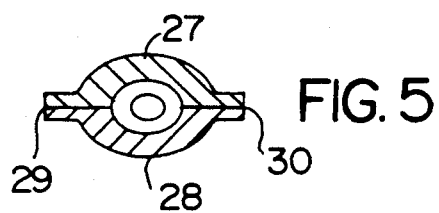
FIG. 5 is a cross-section taken at line 5—5 in FIG. 4.

A cervical pessary 10 according to this invention is shown in FIG. 1. It is intended to be emplaced in the neck of the cervix, with its distal end 11 inside the uterus, its stem 12 in the neck, and its proximal end 13 in the vagina. The purpose of the pessary is to prevent passage of fluid into the uterus. Of course it will also prevent passage of fluid from the uterus.

While contact of the stem with the wall of the cervical passage can prevent passage of fluid, this will generally not be the primary blockage. Instead a distal inflatable retainer 15 and a proximal inflatable retainer 16 are provided. These are hollow, flexible balloon-like members, whose walls are continuous. A passage 17 through the stem fluidly interconnects the inside regions of the retainers.

The walls of the retainers can have thicknesses which are different from one another, or which differs between regions on the same retainer. For example, region 20 of the proximal retainer might be thicker than its central region can balloon more readily as will later be discussed.

The region 22 of the distal retainer might be made thinner than its central region 23 to encourage fluid-tightness against the wall of the uterus. The central region 23 must be flexible enough to deform to permit emplacement, but depending on the objective, it may be either thinner, thicker, or the same as region 22.

A fill valve 25 is fitted in an aperture 26 in the proximal retainer. The purpose of this fill valve is to act as a check valve closure for this aperture. While various other types of valves can be used, a leaflet type valve comprising a pair of flat leaflets 27, 28 in flat adjacency joined along edge seams 29, 30 is quite useful. Return flow is prevented, because the pressure exerted by reversing flowing fluid is stopped by its pressing the leaflets together.

To fill or deflate the pessary, and to emplace it, a fill tube 35 is provided. This is a hollow tube with a central passage 36 and a polished end 37. Side probes 38 pass through the wall of the fill tube into the central passage.

The pessary is shown in its uninflated condition if FIG. 1. To emplace it, the fill tube is pressed through the fill valve and against the central region of the distal retainer. This stretches the distal retainer, and the dimensions are such that the fill tube can thrust the pessary into the correct position. Then fluid is injected into the pessary through the fill tube, withdrawing the tube as appropriate. When the pessary is suitably inflated, the fill tube will be fully withdrawn. The central portion of the proximal retainer is distended, and its roundness can be tactily assured.

The fill valve remains closed and the fluid remains trapped. To deflate and remove the pessary, the fill tube is thrust through the fill valve and fluid is withdrawn, perhaps by aspiration. The deflated pessary can be pulled out with little effort.

Should additional sealing or retention be desired in the stem region, an optional inflatable sleeve 50 can be placed among the stem (FIG. 7). If desired it can be peripherally attached by several seams to form ribs 51, 52, 53 when inflated by fluid which passes through ports 54 in the stem when the pessary is inflated.

This device can readily be made of materials accepted by the body of the type generally used for implants, for example medical grade silicones, or polyurethane. Conveniently, much of the construction can be made by dipping a mandrel into the uncured material, curing the material, and stripping it off of the mandrel.

The requisite dimensions depend on the wearer, and various sizes can be expected to be required for various users.

The fluid used for inflation will usually be normal saline solution because it is acceptable to the body in case the pessary bursts or leaks. Other fluids can of course be used instead.

This invention thereby provides a simple and reliable pessary for its intended purpose which can be made economically, and which provides a high degree of reassurance to its users.

This invention is not to be limited by the embodiment shown in the drawings and described in the description, which is given by way of example and not of limitations, but only in accordance with the scope of the appended claims.

I claim:

1. A cervical pessary having a central stem with a central passage from end to end thereof; a distal retainer at one end, and a proximal retainer at the other end, said retainers formed by walls which are hollow, flexible and distensible, and connected to one another through the central stem passage, said retainers being inflatable by fluid injected into them to extend laterally beyond said stem and abut against the uterus wall and the cervix to close the cervical passage with the stem being disposed in said cervical passage, and a fill valve in said proximal retainer, passing through an aperture in the wall of the proximal retainer, said valve comprising a pair of attached leaflets forming a passage between them, wherein said passage closes when outside pressure is exerted on said leaflets and said leaflets can physically be opened by insertion of a fill tube therein.

2. A cervical pessary according to claim 1 in which a central region of said proximal retainer is so proportioned and arranged as to be palpably enlarged when the pessary is filled with fluid.

3. A cervical pessary according to claim 2 in which a peripheral sleeve surrounds said stem forming a closed chamber between said sleeve and said stem, and in which a port through the stem connects said chamber to said stem passage whereby to distend said sleeve into firmer contact with the cervical passage.

4. A cervical pessary according to claim 3 in which said sleeve is peripherally attached to said stem in a plurality of places whereby to form a plurality of protrusions to engage the cervical passage.

5. In combination: a cervical pessary according to claim 1; and a fill tube insertable into said fill valve to enable the injection and withdrawal of fluid into the pessary, and to engage and distort the distal retainer to stretch it to dimensions which can pass through the cervical passage.

* * * * *